(12) United States Patent
Fortin et al.

(10) Patent No.: US 11,426,087 B2
(45) Date of Patent: Aug. 30, 2022

(54) METHOD AND MEASURING SYSTEM FOR CONTINUOUSLY DETERMINING THE INTRA-ARTERIAL BLOOD PRESSURE

(71) Applicant: CNSYSTEMS MEDIZINTECHNIK AG, Graz (AT)

(72) Inventors: Jürgen Fortin, Graz (AT); Andrea Fortin, Graz (AT); Klaus Popp, Windischgarsten (AT)

(73) Assignee: CNSYSTEMS MEDIZINTECHNIK AG, Graz (AT)

( * ) Notice: Subject to any disclaimer, the term of this patent is extended or adjusted under 35 U.S.C. 154(b) by 700 days.

(21) Appl. No.: 16/078,743

(22) PCT Filed: Feb. 22, 2016

(86) PCT No.: PCT/AT2016/050035
§ 371 (c)(1),
(2) Date: Nov. 7, 2018

(87) PCT Pub. No.: WO2017/143366
PCT Pub. Date: Aug. 31, 2017

(65) Prior Publication Data
US 2019/0150765 A1    May 23, 2019

(51) Int. Cl.
*A61B 5/021* (2006.01)
*A61B 5/0225* (2006.01)
(Continued)

(52) U.S. Cl.
CPC ...... *A61B 5/02255* (2013.01); *A61B 5/02141* (2013.01); *A61B 5/02241* (2013.01);
(Continued)

(58) Field of Classification Search
CPC ............ A61B 5/02255; A61B 5/02241; A61B 5/02141; A61B 5/6826; A61B 2560/0425; A61B 5/022; A61B 5/0225
See application file for complete search history.

(56) References Cited

U.S. PATENT DOCUMENTS 3,229,685 A    1/1966  Ringkamp et al.
4,406,289 A    9/1983  Wesseling et al.
(Continued)

FOREIGN PATENT DOCUMENTS

AT    412613 B    5/2005
JP    H06-125882 A    5/1994
(Continued)

OTHER PUBLICATIONS

International Search Report and Written Opinion for Int. App. No. PCT/AT2016/050035, dated Nov. 23, 2016.

*Primary Examiner* — Meredith Weare
(74) *Attorney, Agent, or Firm* — McDonnell Boehnen Hulbert & Berghoff LLP (57) ABSTRACT

The invention describes a measuring system for the continuous non-invasive determination of blood pressure at one or more fingers. The fingers chosen for measurement and the adjacent parts of the palm rest on a supporting surface of a housing, which has the shape of a computer mouse. Inside the housing of the "CNAP Mouse", i.e. underneath the supporting surface for the hand, the pressure generating system is located. The finger sensors are mounted on the supporting surface for the hand. The forearm and the back of the hand are left free and may be used to place intra-venous or intra-arterial access elements. Since the hand will rest on the supporting surface motion artefacts are largely avoided. Tilting or turning of the sensors is hardly possible since the fit of the sensors and thus the coupling of light and pressure are optimized.

6 Claims, 7 Drawing Sheets

(51) Int. Cl.
*A61B 5/00* (2006.01)
*A61B 5/022* (2006.01)
*A61B 5/0235* (2006.01)

(52) U.S. Cl.
CPC .............. *A61B 5/6826* (2013.01); *A61B 5/70* (2013.01); *A61B 5/0235* (2013.01); *A61B 5/6897* (2013.01); *A61B 2560/0425* (2013.01); *A61B 2562/04* (2013.01)

(56) References Cited

U.S. PATENT DOCUMENTS

| | | | |
|---|---|---|---|
| 4,524,777 A | 6/1985 | Kisioka et al. | |
| 4,726,382 A | 2/1988 | Boehmer et al. | |
| 5,184,359 A * | 2/1993 | Tsukamura | A61B 5/02241 4/314 |
| 5,218,966 A * | 6/1993 | Yamasawa | A61B 5/02141 600/480 |
| 5,511,551 A * | 4/1996 | Sano | A61B 5/02241 600/499 |
| 5,735,798 A * | 4/1998 | Shinohara | A61B 5/022 4/314 |
| 2005/0148885 A1* | 7/2005 | Tweed | A61B 5/411 600/490 |
| 2006/0195034 A1* | 8/2006 | Skrabal | A61B 5/02255 600/485 |
| 2011/0015504 A1* | 1/2011 | Yoo | G16H 40/63 600/301 |
| 2011/0320216 A1* | 12/2011 | Kasmark | G16H 40/67 705/2 |
| 2012/0059233 A1* | 3/2012 | Huber | A61B 5/02255 600/323 |
| 2014/0114152 A1* | 4/2014 | Fournier | A61B 5/6826 600/324 |
| 2014/0142434 A1* | 5/2014 | Nitzan | A61B 5/0261 600/473 |
| 2015/0201852 A1* | 7/2015 | Fortin | A61B 5/02255 600/480 |
| 2016/0192856 A1* | 7/2016 | Lee | A61B 5/0006 600/384 |
| 2016/0198955 A1* | 7/2016 | Fortin | A61B 5/02225 600/323 |
| 2021/0307632 A1* | 10/2021 | Scheuermann | A61B 5/02255 |

FOREIGN PATENT DOCUMENTS

| | | |
|---|---|---|
| JP | H07-308297 A | 11/1995 |
| JP | H09-24029 A | 1/1997 |
| JP | H10-312241 A | 11/1998 |
| JP | 3486976 B2 | 1/2004 |
| KR | 2010-0042566 A | 4/2010 |
| WO | 2000/059369 A2 | 10/2000 |
| WO | 2004/086963 A2 | 10/2004 |
| WO | 2005/037097 A1 | 4/2005 |
| WO | 2007/028107 A2 | 3/2007 |
| WO | 2010/050798 A1 | 5/2010 |
| WO | 2011/045138 A1 | 4/2011 |
| WO | 2011/051819 A1 | 5/2011 |
| WO | 2011/051822 A1 | 5/2011 |
| WO | 2012/032413 A2 | 3/2012 |
| WO | WO-2013178475 A1 * 12/2013 ......... A61B 5/02116 |

\* cited by examiner

Fig. 1
(State of the Art)

METHOD AND MEASURING SYSTEM FOR CONTINUOUSLY DETERMINING THE INTRA-ARTERIAL BLOOD PRESSURE

CROSS REFERENCE TO RELATED APPLICATIONS

The present application is a U.S. National Phase Application pursuant to 35 U.S.C. § 371 of International Application No. PCT/AT2016/050035 filed Feb. 22, 2016. The entire disclosure content of this application is herewith incorporated by reference into the present application.

BACKGROUND

The invention relates to a method and a measuring system for continuously determining the intra-arterial blood pressure at one or more fingers of a hand by means of a finger sensor. The sensor comprises a plethysmographic system with at least one light source, at least one light receiver or light detector, and at least one inflatable cuff. Further there is provided a pressure generating system with at least one valve, which is controlled in real time by the plethysmographic system for generating pressure in the cuff, the pressure essentially corresponding to the intra-arterial blood pressure in the finger.

Continuous non-invasive measurement of blood pressure presents even today a serious challenge to measuring technology. The so-called "Vascular Unloading Technique" is beginning to dominate the market. This technique is based on a publication by Penáz (Digest of the $10^{th}$ International Conference on Medical and Biological Engineering, 1973 Dresden) and has been improved by diverse enhancements.

The Vascular Unloading Technique begins with shining light through a finger, thus determining the pulsatile (pulse-shaped) blood flow in the finger. This method is called photo-plethysmography (PPG) and is usually implemented with the use of one or more light-emitting diodes (LEDs) working at one or more wavelengths, and one or more light-sensitive receiving diodes (photo diodes).

A control system keeps the registered flow and thus the resulting PPG signal (volume signal v(t)) constant by applying counter pressure in a cuff (cuff pressure $p_c(t)$) around the finger. This counter pressure $p_c(t)$ is generated via a fast valve or valve system fed by a pump. The valve or valve system is controlled by the control unit, which preferably is realized as a microcomputer. The essential input signal is the PPG signal v(t), in more recent control systems the cuff pressure $p_c(t)$ is used as an additional input variable. The pressure $p_c(t)$ necessary to keep the flow or rather the PPG signal v(t) constant thus corresponds to the intra-arterial blood pressure $p_a(t)$.

In order to fulfill the real-time condition it is necessary that the cuff pressure $p_c(t)$ can be varied at least as fast as the intra-arterial blood pressure $p_a(t)$ changes. For complete fulfillment of this control condition the cuff pressure $p_c(t)$ must be able to mimic the intra-arterial pressure $p_a(t)$ in the time domain as well as in the frequency domain. The upper frequency limit of $p_a(t)$ and thus the highest rate of change of the pressure lies upwards of at least 20 Hz, presenting a serious challenge for the pressure system. As a consequence pressure generation via a valve or valve system must be located in the immediate vicinity of the cuff. If long air tubes are used the frequency limit condition cannot be met due to the low-pass characteristic of the tubes. In all known devices commercially available or described in publications, the valve or valve system or pressure generating system is therefore located on the distal forearm next to the wrist, either on the upper side or underside of the arm.

Placing the pressure generating system on the distal forearm next to the wrist has serious disadvantages: this site is often chosen for intravenous access points and intra-arterial access should also be possible at the distal end of radius in cases of emergency. These access points would be blocked by the pressure generating system and its fastening elements. The system might also slip or tilt during operation. This might have an adverse effect on the positioning of the sensors. Positioning of the sensors would moreover be improved if the finger to be measured or the corresponding hand could be held in a state of rest.

A large number of publications concerning the Vascular Unloading Technique are known: U.S. Pat. No. 4,406,289 (Wesseling et al.) describes a mechanical valve which generates the counter pressure in the finger cuff with desired accuracy if fed by a linear pump. The valve is placed in a housing at the distal forearm and supplies pressure $p_c(t)$ to the finger cuff via a short tube.

U.S. Pat. No. 4,524,777 (Kisioka et al.) describes a pressure generating system for the Vascular Unloading Technique. A constant cuff pressure $P_c$ is first generated by a linear pump on which pressure fluctuations $\Delta p_c(t)$ are superimposed, which are supplied by a "shaker" or "driving actuator" connected in parallel.

U.S. Pat. No. 4,726,382 (Boehmer et al.) describes a finger cuff for the Vascular Unloading Technique, which has tube fittings for supplying the cuff pressure $p_c(t)$. The length of the tubes is sufficient to reach the pressure generation system (not shown) placed on the distal forearm.

WO 2000/059369 (Fortin et al.) also describes a pressure generating system for the Vascular Unloading Technique. The valve system consists of a separate inlet and a separate outlet valve. While U.S. Pat. Nos. 4,406,289 and 4,524,777 require a relatively linear proportional pump, this system permits the use of simple, less costly pumps, since noxious harmonics are eliminated due to the arrangement of the valves. Furthermore the energy required for the simple pump is substantially reduced due to the valve principle.

WO 2004/086963 (Skrabal et al.) describes a system for the Vascular Unloading Technique, in which blood pressure can be continuously measured in one finger, while the adjacent finger ("Watch Dog") is used for quality control. After a certain time the system automatically exchanges the "measurement finger" and the "supervisor finger".

WO 2005/037097 (Fortin et al.) describes a control system for the Vascular Unloading Technique, in which a plurality of nested control loops provide for high frequency pressure variation and long time stability of accuracy.

WO 2010/050798 (Guelen et al.) essentially describes a pressure generation system attached to the distal forearm ("Frontend") with only one valve that can be connected to a finger cuff for the Vascular Unloading Technique.

WO 2011/045138 (Langewouters et al.) describes a pressure generation system for the Vascular Unloading Technique, where—similar to WO 2000/059369—energy consumption of the pump is reduced and harmonics are eliminated.

WO 2011/051819 (Fortin et al.) describes a novel kind of Vascular Unloading Technique entirely implemented by digital electronics, with improved stability and further miniaturization.

WO 2011/051822 (Fortin et al.) describes a method for the Vascular Unloading Technique, in which the measured signals v(t) and $p_c(t)$ are processed such that long term stability is improved and further hemodynamic parameters can be obtained. In particular, a method for eliminating vasomotoric fluctuations of the finger arteries and a method for determining the cardiac output are described.

WO 2012/032413 (Huber et al.) describes a novel kind of finger sensors with a disposable part.

SUMMARY

It is the object of the present invention, given a measuring system for continuous non-invasive determination of intra-arterial blood pressure as initially described, to propose improvements enhancing the patient's wearing comfort and to avoid tiring hand positions during lengthy measurement periods.

According to the invention this object is achieved by providing that the measuring system has a housing with a surface which may serve as a supporting surface for the at least one finger and adjacent parts of the palm. Preferably the housing of the measuring system should essentially have the dimensions and the outer shape of a computer mouse, with the at least one finger sensor projecting from the supporting surface for the hand.

A measuring method according to the invention using a plethysmographic system and a pressure generating system controlled by the plethysmographic system, is characterized in that the finger or fingers chosen for measurement are introduced into the inflatable cuff and, to ease tension in the hand, are placed on a supporting surface of a housing together with adjacent parts of the palm, which housing contains the pressure generating system.

The present invention combines the finger sensor, i.e. the finger cuff and its light generating system, and the pressure generating system, thereby avoiding the disadvantages cited above. The fingers chosen for measurement and the respective hand rest on a supporting surface beneath which the pressure generating system is located. One or more finger sensors, i.e. the finger cuffs including the PPG system, are disposed on the supporting surface for the hand. The forearm and the back of the hand are free and thus available for intra-venous or intra-arterial access points. Since both the fingers used for measurement and the hand rest on the supporting surface, artefacts due to motion are reduced. Turning or tilting of the sensors is hardly possible as the positioning of the sensors and thus the coupling of light and pressure are optimized.

Since the hand will rest on the supporting surface like on a computer mouse, the system is called CNAP Mouse (Continuous Non-invasive Arterial Pressure). The body or the housing of the "mouse" contains at least the pressure generating system for the Vascular Unloading Technique. The "ears" of the CNAP mouse are represented by the usually two finger sensors (cuffs including the PPG system). Two finger sensors are used to permit a longer period of measurement by interchanging the role of the fingers; while one finger is used for measuring continuous blood pressure, the other finger is at rest. The CNAP mouse of course also works with only one "ear", i.e. with only one finger sensor.

The invention will now be described in more detail, with reference to schematically presented exemplary embodiments.

DETAILED DESCRIPTION

The invention describes a measuring system for the continuous non-invasive determination of blood pressure. The combination of pressure generating system and finger sensors comprising cuff and light system—the photoplethysmographic system—is presented in detail.

In principle the Vascular Unloading Technique mimics the intra-arterial pressure in the finger cuff in real time. This is done by means of a control system which requires as input signal at least the light signal v(t) of the PPG system. More recent control systems, such as described in publications WO 2000/059369, WO 2005/037097, WO 2011/0511819 or WO 2011/051822, also use the cuff pressure $p_c(t)$ as an input variable.

The pressures obey the following equation, which arises when the air-filled cuff is applied:

$$p_c(t) = p_a(t) - p_t(t) \quad (1)$$

where $p_t(t)$ is the socalled "transmural pressure", i.e. the pressure difference between cuff pressure $p_c(t)$ and intra-arterial blood pressure $p_a(t)$.

The transmural pressure $p_t(t)$ acts on the diameter of the artery, which diameter can indirectly be determined from the PPG signal or volume signal v(t). As has been described above, the control system will adapt the cuff pressure $p_c(t)$ in real time such that v(t) will be kept constant, i.e. that Δv(t)=0. If this condition Δv(t)=0 is fulfilled, the transmural pressure $p_t(t)$=0, and therefore one has $$p_c(t) = p_a(t) - 0 \quad (2)$$

In order to fulfil this real-time condition, the measuring system must be able to follow the changes in intra-arterial blood pressure $p_a(t)$. Interpreting the control condition in the frequency domain the measuring system must be able to mimic pressure changes which transcend the upper limit frequency of intra-arterial blood pressure. This upper limit freqency of intra-arterial blood pressure $p_a(t)$ lies approximately at 20 Hz.

All the methods and devices described require that the cuff pressure $p_c(t)$ must be available over the total relevant frequency range with an upper limit frequency of at least 20 Hz, a requirement which presents a challenge to the pressure generating system and its valves or valve system. It is therefore important that the pressure generating system and its valve or valve system be situated in the immediate vicinity of the finger cuff. Depending on the rigidity of the connecting tube, the maximum distance will be 30 to 50 cm.

Figure 1:
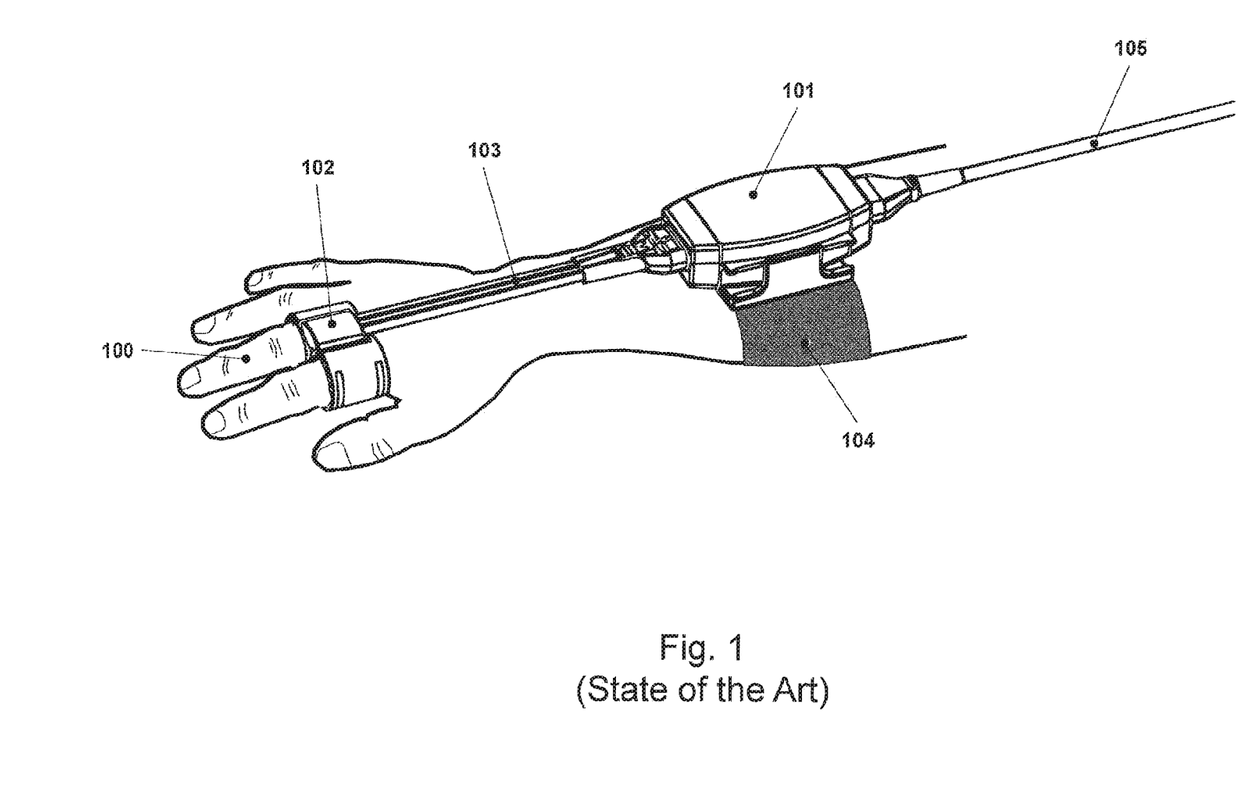
FIG. 1 shows a state-of-the-art measuring system, where the pressure generating system is placed at the distal end of the forearm.

FIG. 1 shows how the pressure system 101 is connected to the finger sensor 102 in a state-of-the-art measuring system. The finger sensor 102 shown is designed as a double finger sensor for index and middle finger 100 of the right hand, permitting longer duration of measurement. The finger sensor 102 is supplied with pressure and electric energy via a double tube system 103. The pressure system 101 is attached to the distal end of the forearm by means of a fastening element 104 and is supplied via a cable 105 with electric energy and with basic pressure.

Figure 2:
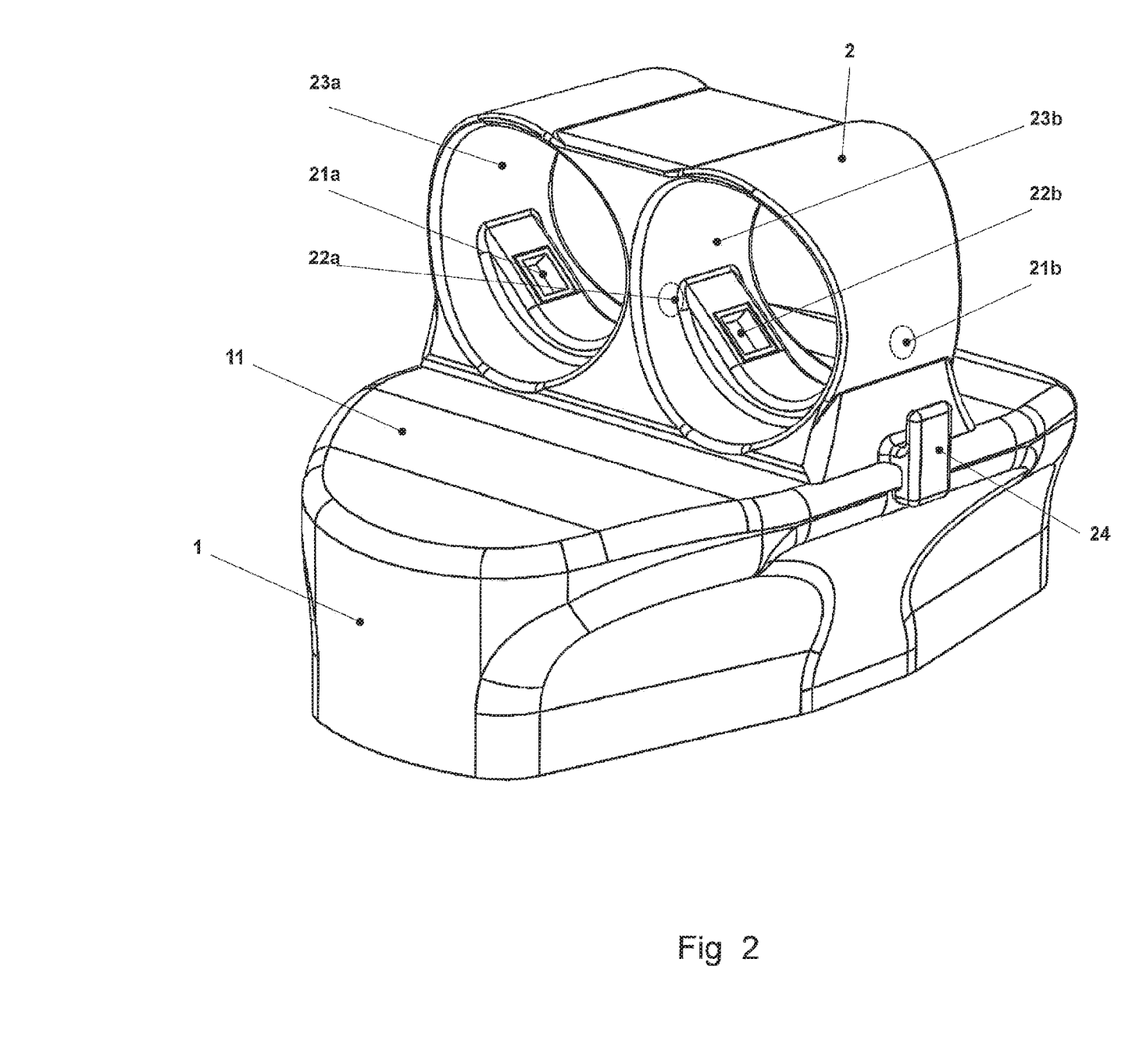
FIG. 2 shows the measuring system according to the invention in the shape of a computer mouse (CNAP mouse) in a three-dimensional view.

FIG. 2 shows the measuring system according to the invention, the assembled CNAP mouse. On the body or on the housing 1 of the CNAP mouse there is provided a relatively large supporting surface 11 upon which the hand may rest during the measuring operation. The finger sensors 2 are attached to the housing 1. In the example there is shown a double finger sensor, with which each finger may be measured alternatingly. The double sensor has two light sources (LEDs) 21a, 21b and at least two light sensors 22a, 22b (partly visible). The two inflatable cuffs 23a and 23b are disposed on the interior areas 23 of the finger sensors 2. The part of the finger sensor 2 which carries the inflatable cuffs 23a, 23b is removable and may be exchanged, and is attached to a locking element on the housing 1 by means of snap-on element 24.

Figure 3:
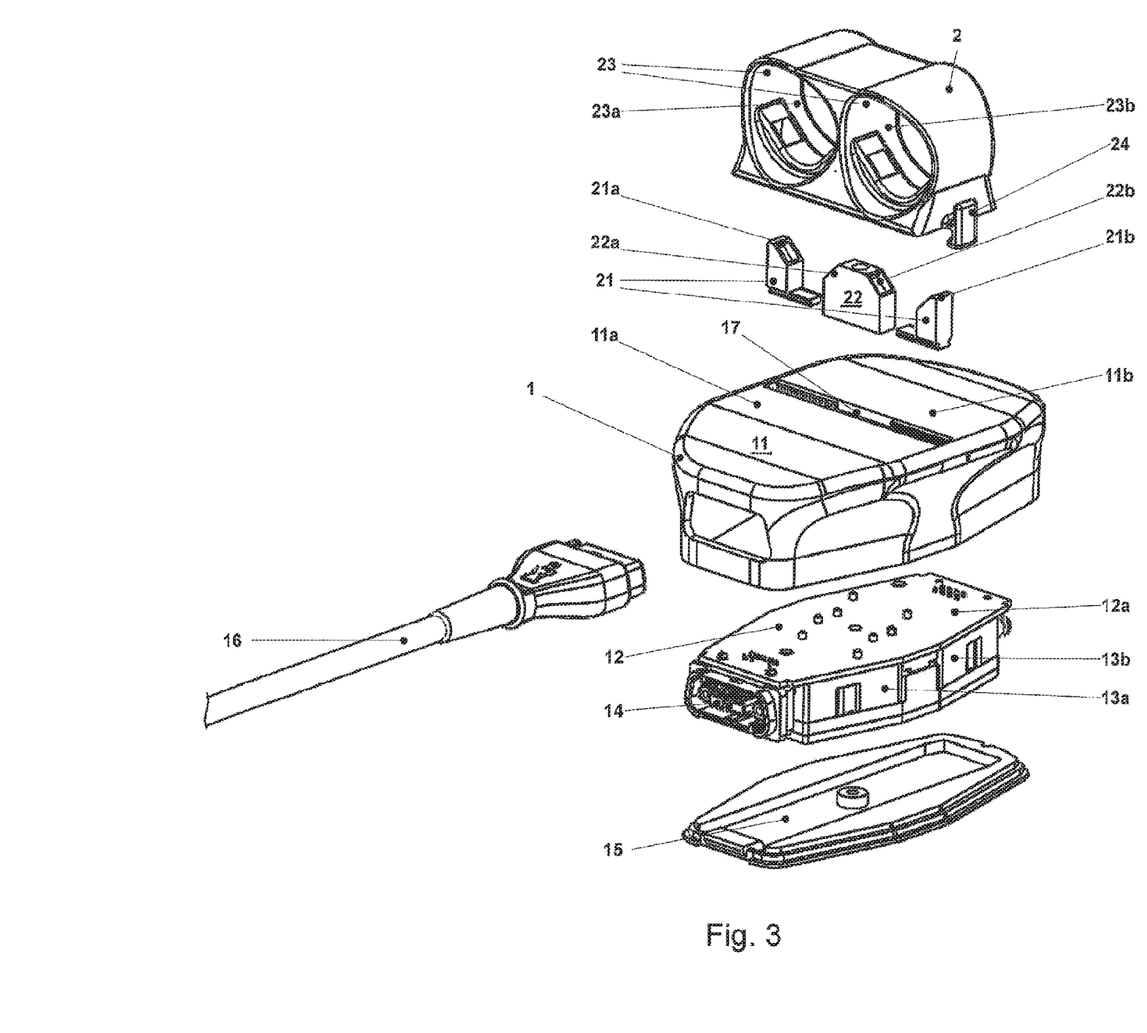
FIG. 3 shows the measuring system of FIG. 2 in an exploded view.

FIG. 3 shows an exploded view of the CNAP mouse. First it is shown how the pressure generating system 12 is integrated into the body or the housing 1 of the mouse underneath the supporting surface 11 for the hand. In this case the pressure generating system 12 consists of an electronic circuit board 12a, which carries one or more valves 13a, 13b as well as the elements of the valve control electronics. Preferably, a connector 14 is also provided on the board 12a. The pressure generating system 12 is placed in the housing 1 and secured by a cover 15 on the bottom of the housing 1. A cable 16 supplies the pressure generating system 12 with basic pressure, electric energy and the signals emitted by the control system for the Vascular Unloading Technique.

On the top face of the housing 1 there are provided fittings for one or more finger sensors. On the one hand these must have electric connectors for the PPG signal, on the other hand there must be provided pressure fittings for supplying pressure to the one or more cuffs. In the variant shown, which presents the double finger system as described above, this is achieved as follows: a receiving slot 17 partitions the top of the body of the mouse 1, which is also the supporting surface 11, into two partial surfaces 11a and 11b. Into this slot two outer slideable elements 21 and a central element 22 are inserted. The slideable elements 21 contain the two LEDs 21a and 21b necessary for generating the PPG signal. The outer elements are movable in order to accommodate various sizes of the finger sensor. The element 22 sits in the middle of the slot and is not movable. It contains the two light detectors 22a and 22b.

Onto this body or housing 1 of the mouse carrying the elements 21, 22 for the PPG signal as shown, the detachable part of the finger sensor 2 may be mounted. The finger sensors may have diverse sizes or diameters. The optimum fit of the sensors may thus be adapted to the actual finger size. The sensors have an air-inflatable cuff 23a, 23b whose pressure can be controlled by the pressure generating system 12 with the required accuracy. For this purpose fitting elements are provided, which are integrated in the element 22 (not explicitly shown). Furthermore the PPG system must be integrated into the sensors. In the case shown this is realized by the double finger sensor 2 already known. The double finger sensor 2 contains on its interior wall 23 a cuff 23a, 23b for each finger. The advantage of the design of the invention lies in the fact that no electrical leads for the PPG system are necessary for the detachable part of the double finger sensor 2 containing the cuffs 23a, 23b. The PPG elements sit on the housing 1 of the mouse and are supplied with electrical power there.

Figure 4:
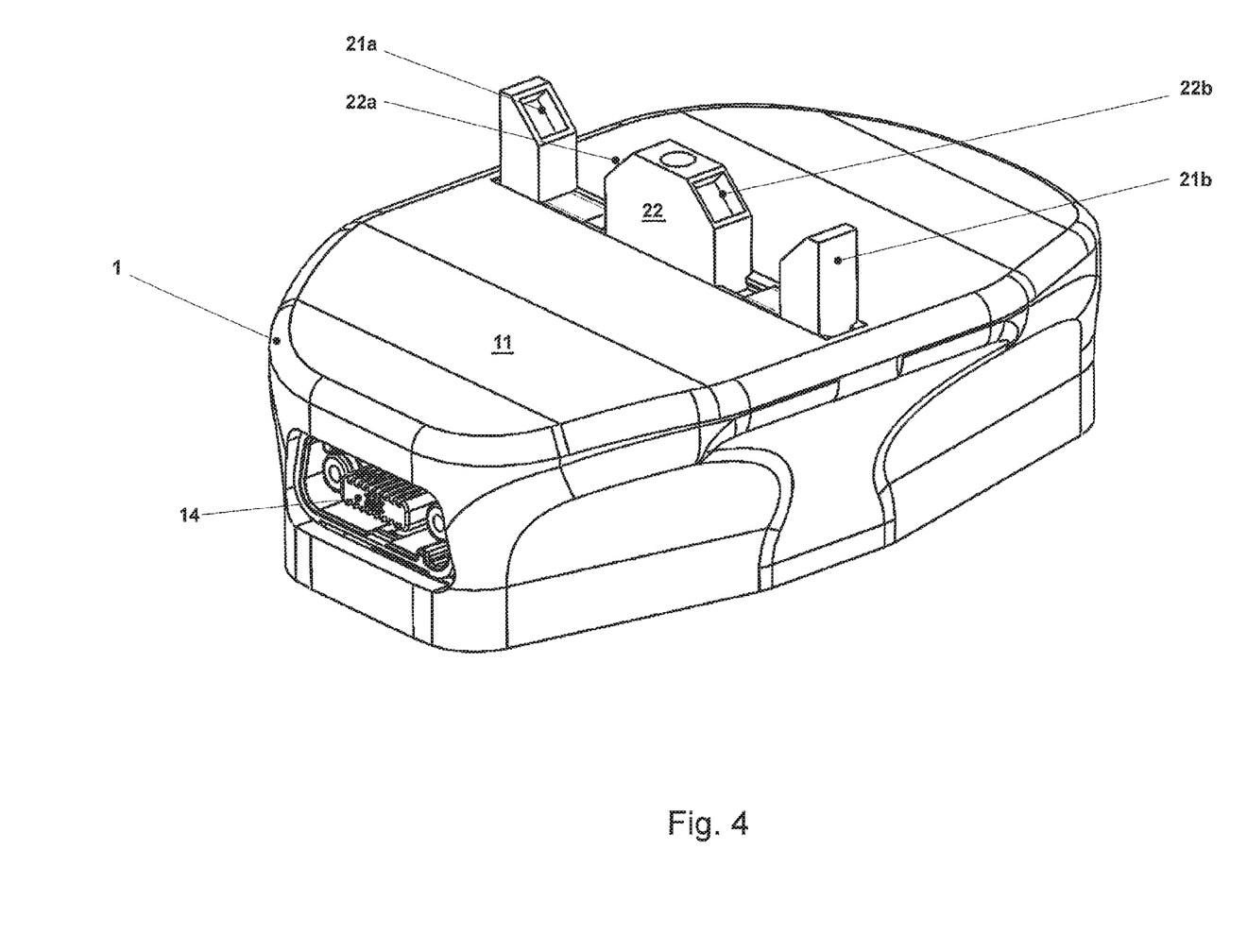
FIG. 4 shows the measuring system of FIG. 2 with the cuff part removed and the PPG elements visible.

FIG. 4 shows how the PPG elements 21a, 21b and 22a, 22b are attached to the housing 1 of the mouse. One can see that the LED elements 21a, 21b are movable in order to adapt to the detachable part of finger sensors of varying size. The element 22 carrying the light detectors 22a, 22b, however, is fixedly attached in the middle of the supporting surface 11. In this variant the connector 14 supplies the CNAP mouse with basic air pressure, electrical energy and control signals.

Figure 5:
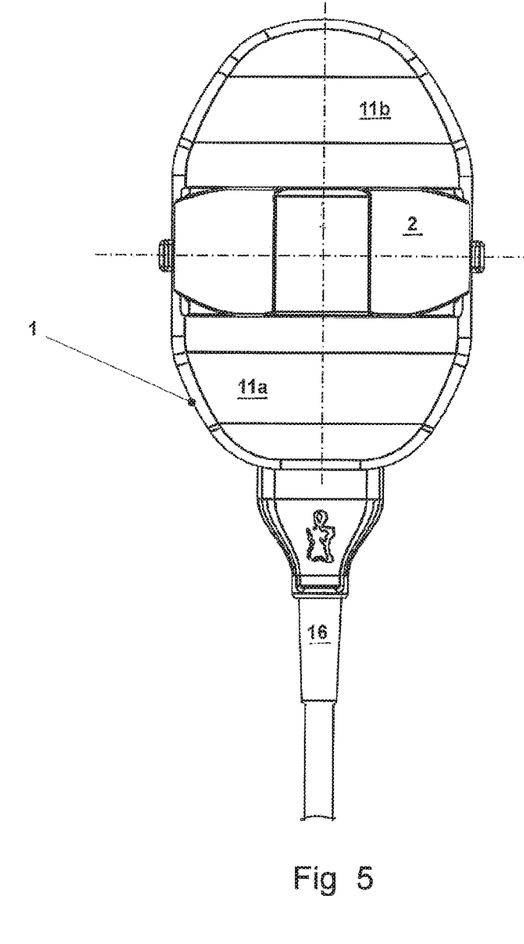
FIG. 5 shows the symmetrical design of the measuring system of FIG. 2 in a top view.

FIG. 5 shows a mirror-symmetrical variant of the invention in a top view. On the housing 1 of the CNAP mouse the finger sensor 2 is attached, which partitions the supporting surface 11 for the hand into two partial surfaces 11a and 11b. The CNAP mouse is supplied via a cable 16 with basic air pressure, electrical energy and the control signals from below (as shown) or proximally as regards the hand. There is no problem in turning the mouse around and supplying it from above or distally as regards the hand.

Figure 6:
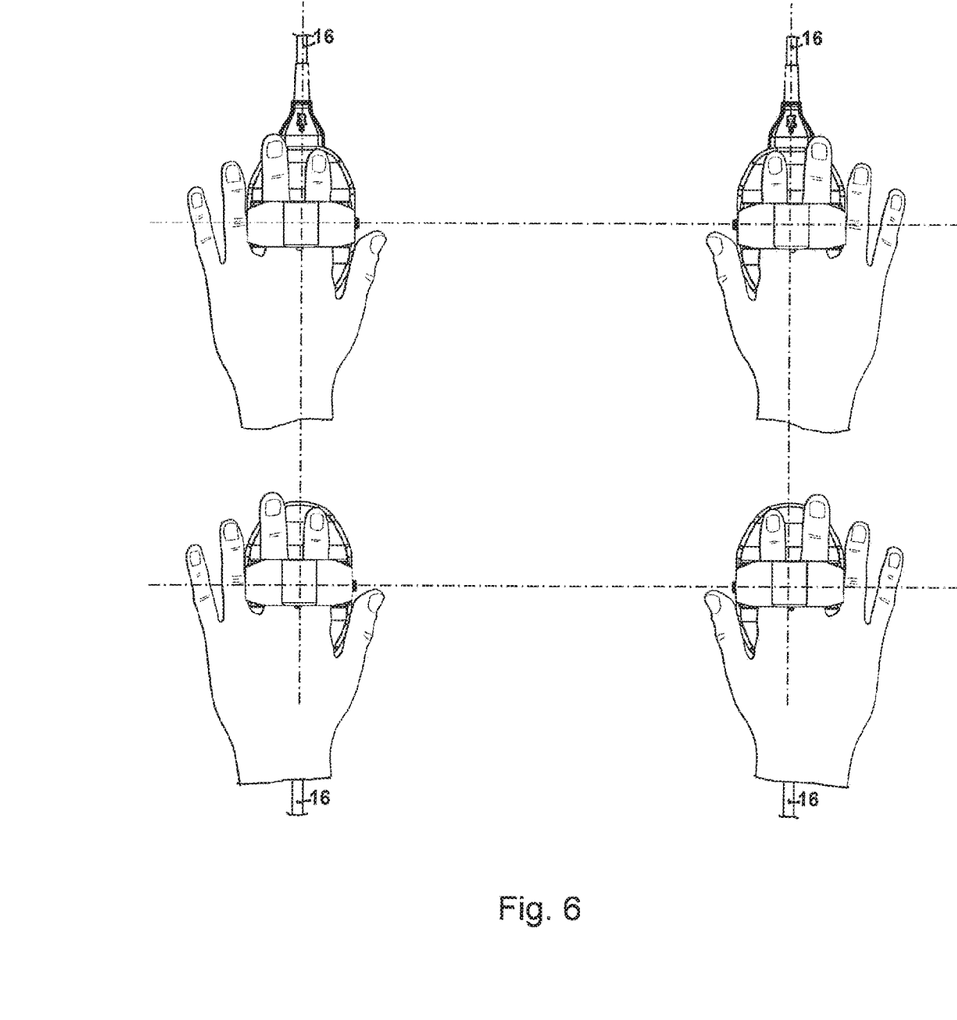
FIG. 6 shows all possible ways of applying the measuring system to the right or left hand of a patient.

FIG. 6 demonstrates the advantage derived from the mirror-symmetrical design of the CNAP mouse. The mouse may be used with the fingers of the left hand as well as with those of the right hand. The pair index finger, middle finger (as shown) may be used, as well as the pair middle finger, third finger (not shown). The mouse may be served by the cable 16 either from behind (proximally as regards the hand) or from in front (distally as regards the hand). This will afford maximum flexibility of application of the device on the patient.

The supporting surface for the hand should preferably be soft, permitting hand and fingers to relax in order to avoid motion artefacts. A cushion or a gel pack may therefore be placed on the supporting surface 11.

Figure 7:
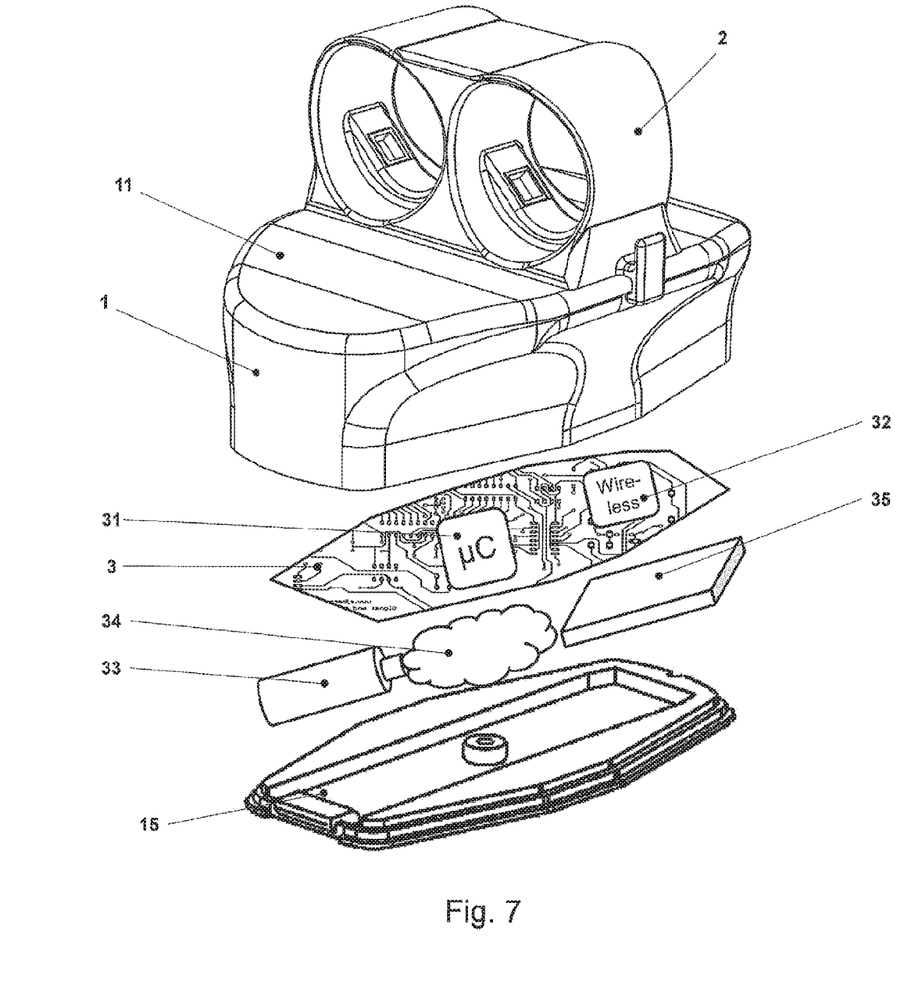
FIG. 7 shows a variant of the measuring system according to the invention in an exploded view.

It is furthermore of advantage if the control system 3 with the microcontroller 31 for fulfilling the real-time condition of the Vascular Unloading Technique is also included in the housing 1 of the CNAP mouse (see FIG. 7). The electronic circuit board of the control system 3 may for instance be disposed underneath the pressure generating system 12. As a result the measuring system need only be supplied with basic pressure and electrical energy.

Carrying this one step farther, it is also possible to integrate a miniature pump 33 in the housing 1 of the mouse. Between the pump 33 and the pressure generating system 12 there is usually an air reservoir 34 disposed, in order to compensate high frequency pressure fluctuations resulting from irregularities in the pump motor. According to one variant this small air reservoir 34 may also be integrated in the body of the mouse (see FIG. 7).

According to a variant of the invention space may be saved in the housing 1 of the mouse by creating an airtight cavity underneath the supporting surface for the hand which can serve as an air reservoir. The electronic circuit board will then be contained in the housing under increased air pressure, but this will not harm the electronic circuits. The air reservoir will thus not require extra volume. In this case the measuring system only has to be supplied with electrical energy.

As a further step of development a power pack or battery 35 may be integrated into the housing 1. Using wireless signal transmission via a wireless chip (see element 32 "wireless" in FIG. 7) the measuring system may function completely independently.

According to the invention it is also possible to attach only a single finger sensor in a corresponding slot on the CNAP mouse, but two individual finger sensors or more would be possible as well. The variant shown in the drawings seems to be of special practical use since the double finger system will permit long measuring times by alternatingly measuring one and the other finger.

The variants cited should be taken as examples only; any variants resulting from permutations of these will also be considered protected.

The invention claimed is:

1. A measuring system for the continuous determination of intra-arterial blood pressure at two fingers of a hand having a palm, the measuring system comprising:
    a double-finger sensor having inflatable cuffs for the two fingers;
    a plethysmographic system comprising at least two light sources, with one or more wavelengths, and at least two light detectors;
    a pressure generating system comprising at least one valve, controlled in real time by the plethysmographic system, for generating pressure in the cuffs, which pressure is available over a frequency range with an upper limit frequency of at least 20 Hz and corresponds to the intra-arterial blood pressure in the finger; and
    a housing comprising:
        an upper supporting surface configured to support the two fingers and adjacent areas of the palm of the hand, the upper supporting surface having a curved outer profile; and
        a flat bottom surface configured to rest on a supporting plane;
    wherein the double-finger sensor projects from the upper supporting surface;
    wherein the upper supporting surface comprises a receiving slot that partitions the upper supporting surface mirror-symmetrically into two partial surfaces, the receiving slot containing elements for connecting the plethysmographic system to the double-finger sensor;
    wherein the elements for connecting the plethysmographic system to the double-finger sensor comprises two outer elements disposed in the receiving slot that are slideable in the direction of a central element;
    wherein a part of the double-finger sensor which accommodates the inflatable cuffs is fastened to the elements in a removable and exchangeable manner;
    wherein the two outer elements contain the two light sources while the central element contains the two light detectors; and
    wherein the pressure generating system with the at least one controlled valve is located in the housing underneath the upper supporting surface.

2. The measuring system according to claim 1, wherein a control system is disposed in the housing underneath the upper supporting surface for the hand.

3. The measuring system according to claim 1, wherein a pump and an air reservoir are disposed in the housing underneath the upper supporting surface for the hand.

4. The measuring system according to claim 1, wherein the housing of the measuring system is made air-tight underneath the upper supporting surface for the hand, and acts as an air reservoir.

5. The measuring system according to claim 1, wherein a battery or a power pack, and elements for wireless transmission of signals are disposed in the housing underneath the upper supporting surface for the hand.

6. A measuring system for the continuous determination of intra-arterial blood pressure at two fingers of a hand having a palm, the measuring system comprising:
    a double-finger sensor having inflatable cuffs for the two fingers;
    a plethysmographic system comprising at least two light sources, with one or more wavelengths, and at least two light detectors; and
    a pressure generating system comprising at least one valve, controlled in real time by the plethysmographic system, for generating pressure in the cuffs, which pressure corresponds to the intra-arterial blood pressure in the finger; and
    wherein the measuring system has a housing comprising:
        an upper supporting surface configured to support the two fingers and adjacent areas of the palm of the hand, the upper supporting surface having a curved outer profile, and
        a flat bottom surface configured to rest on a supporting plane,
    wherein the double-finger sensor projects from the upper supporting surface;
    wherein two outer elements are disposed in a receiving slot on the upper supporting surface of the housing so as to be slideable in the direction of a central element;
    wherein a part of the double-finger sensor which accommodates the inflatable cuffs is fastened to the elements in a removable and exchangeable manner; and
    wherein the two outer elements contain the two light sources while the central element contains the two light detectors.

* * * * *